US00PP30116P2

(12) United States Plant Patent
Ren

(10) Patent No.: US PP30,116 P2
(45) Date of Patent: Jan. 15, 2019

(54) ***ECHINACEA* PLANT NAMED 'BALSOMEMYIM'**

(50) Latin Name: *Echinacea x hybrida*
Varietal Denomination: Balsomemyim

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/732,053

(22) Filed: Sep. 11, 2017

(51) Int. Cl.
*A01H 5/02* (2018.01)

(52) U.S. Cl.
USPC ..... Plt./428

(58) Field of Classification Search
USPC ..... Plt./428
CPC . A01H 5/025; A01H 5/02; A01H 5/00; A01H 6/14
See application file for complete search history.

(56) References Cited

U.S. PATENT DOCUMENTS

PP24,768 P2 * 8/2014 Ren ..... A01H 6/14
Plt./428

OTHER PUBLICATIONS

Ball Seed Plant Information *Echinaceae* Sombrero Lemon Yellow Improved 2018, retrieved on Jul. 23, 2018, retrieved from the Internet at https://ballseed.com/PlantInfo/?phid=024102187037101, one page. (Year: 2018).*

Gully Greenhouse 2018 Young Plant, retrieved on Jul. 23, 2018, retrieved from the Internet at https://2mruyd4785fe1dwfqe1jnn9l-wpengine.netdna-ssl.com/wp-content/uploads/2017/06/2018-Gulley-Young-Plant-Catalog.pdf, 2 pp. introductory, pp. 1-7, 11, 12, 32 and back cover page. (Year: 2017).*

* cited by examiner

*Primary Examiner* — June Hwu
(74) *Attorney, Agent, or Firm* — Audrey Charles

(57) ABSTRACT

A new and distinct cultivar of *Echinacea* plant named 'Balsomemyim', characterized by its single-type, dark yellow-colored inflorescences, medium green-colored foliage, and moderately vigorous, compact-upright growth habit, is disclosed.

1 Drawing Sheet

Latin name of genus and species of plant claimed: *Echinacea* x *hybrida*.

Variety denomination: 'Balsomemyim'.

BACKGROUND OF THE INVENTION

The present invention relates to a new and distinct cultivar of *Echinacea* plant botanically known as *Echinacea* x *hybrida* and hereinafter referred to by the cultivar name 'Balsomemyim'.

The new cultivar originated in a controlled breeding program in Elburn, Ill. during October 2012. The objective of the breeding program was the development of *Echinacea* cultivars with a single inflorescence form having imbricate ray florets and a well-branched, compact growth habit.

The new *Echinacea* cultivar is the result of cross-pollination. The female (seed) parent of the new cultivar is the proprietary *Echinacea* x *hybrida* breeding selection coded E97-6-12, not patented, characterized by its single-type, dark yellow-colored ray florets, medium green-colored foliage, and moderately vigorous, semi-upright growth habit. The male (pollen) parent of the new cultivar is from a bulk pollen mix of thirteen proprietary *Echinacea* x *hybrida* breeding selections coded E97-6-1 through E97-6-13, not patented, characterized by their single-type, dark yellow-colored ray florets, medium green-colored foliage, and moderately vigorous, semi-upright growth habit. The new cultivar was discovered and selected as a single flowering plant within the progeny of the above stated cross-pollination during October 2013 in a controlled environment in Elburn, Ill.

Asexual reproduction of the new cultivar by in vitro shoot propagation since October 2013 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsomemyim' as a new and distinct cultivar of *Echinacea* plant:

1. Single-type, dark yellow-colored inflorescences;
2. Medium green-colored foliage; and
3. Moderately vigorous, compact-upright growth habit.

Plants of the new cultivar differ from plants of the female and possible male parents primarily in having a slightly different ray floret color and a more compact habit.

Of the many commercially available *Echinacea* cultivars, the most similar in comparison to the new cultivar is SOMBRERO Lemon Yellow 'Balsomemy', U.S. Plant Pat. No. 24,768. However, in side by side comparisons, plants of the new cultivar differ from plants of 'Balsomemy' in at least the following characteristics:

1. Plants of the new cultivar have a ray floret color that is slightly darker than plants of 'Balsomemy';
2. Plants of the new cultivar have a receptacle spine color that is more yellow than plants of 'Balsomemy'; and
3. Plants of the new cultivar have longer ray florets than plants of 'Balsomemy'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsomemyim'. The plants were approximately 18-weeks old and grown in Elburn, Ill. in one-gallon containers for approximately 4 weeks in a greenhouse and 6 weeks outdoors.

DETAILED BOTANICAL DESCRIPTION

Figure 1:
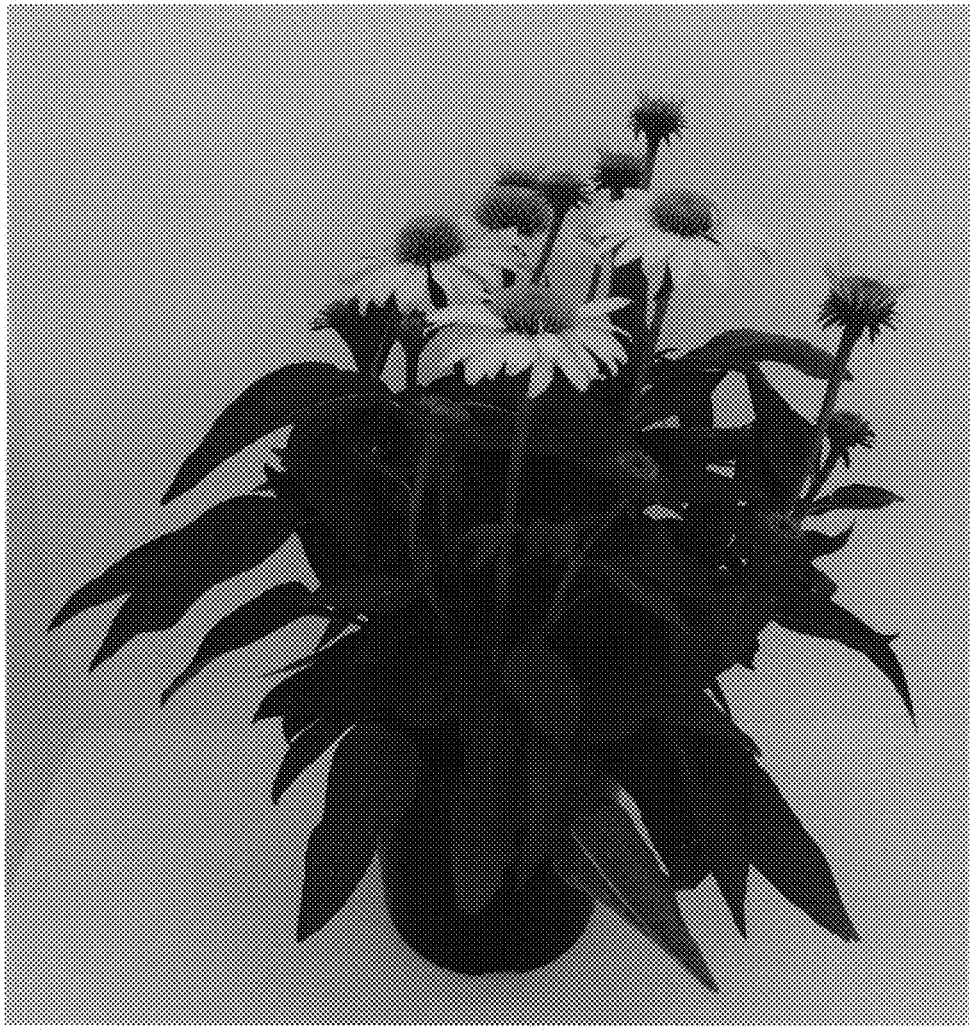
FIG. 1 illustrates a side view of the overall growth and flowering habit of 'Balsomemyim'.
Figure 2:
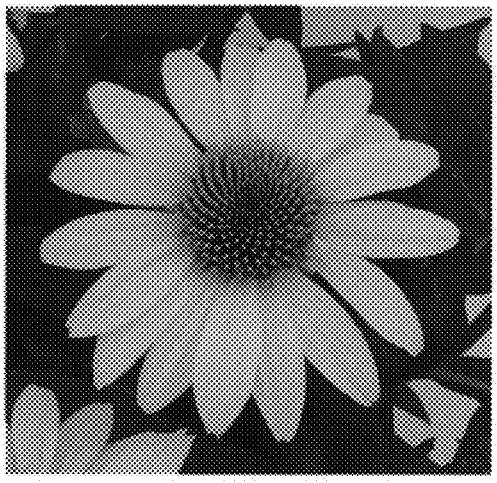
FIG. 2 illustrates a close-up view of an individual inflorescence of 'Balsomemyim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2017 under natural light conditions in West Chicago, Ill.

The following descriptions and measurements describe approximately 18-week old plants produced from in vitro plantlets and grown utilizing a soilless growth medium under conditions comparable to those used in commercial practice. The plants were grown in Elburn, Ill. in one-gallon containers in a glass-covered greenhouse for approximately 4 weeks and then outside for approximately 6 weeks. Greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Echinacea* x *hybrida* 'Balsomemyim'.

Parentage:

*Female parent*.—Proprietary *Echinacea* x *hybrida* breeding selection coded E97-6-12, not patented.

*Male parent*.—Bulk pollen mix of five proprietary *Echinacea* x *hybrida* breeding selections coded E97-6-1 through E97-6-13, not patented.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 10 to 12 weeks from a rooted tissue culture plantlet to finish in a 15 cm container.

*Growth habit and general appearance*.—Herbaceous perennial, moderately vigorous, compact-upright.

*Hardiness*.—USDA Zone 5a (−20° F. to −15° F./−28.9° C. to −26° C.).

*Size*.—Height from soil level to top of plant plane: Approximately 33.0 cm. Width: Approximately 42.0 cm.

*Branching habit*.—No lateral branching, flowering stems grow from base. Quantity of main stems per plant: Approximately 7.

*Stems*.—Strength: Very strong. Aspect: Nearly erect. Shape: Rounded. Length to base of inflorescence: Approximately 25.0 cm. Diameter: Approximately 6.0 mm. Length of central internode: Approximately 3.0 cm. Texture: Densely pubescent with short strigose hairs. Color of young and mature stems: 144A to 144B.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 11.5 cm. Width of mature leaf: Approximately 4.7 cm. Texture of upper surface: Dull, moderately pubescent with short strigose hairs. Texture of lower surface: Moderately pubescent with short strigose hairs. Color of upper surface of young and mature foliage: Closest to 137A with venation of 147C. Color of lower surface of young and mature foliage: Closest to 147B with venation of 147C.

*Petiole*.—Shape: V-shaped. Length: Approximately 7.0 cm. Diameter: Approximately 4.0 mm. Texture of upper surface: Glabrous. Texture of lower surface: Sparsely covered with very short strigose hairs. Color of upper and lower surfaces: 147C.

Flowering description:

*Flowering habit*.—'Balsomemyim' is freely flowering under outdoor growing conditions blooming from spring through autumn and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 4. Height: Approximately 3.5 cm. Diameter: Approximately 9.5 cm.

*Peduncle*.—Strength: Strong. Aspect: Erect to approximately 45° from vertical. Length: Approximately 11.0 cm. Diameter: Approximately 5.0 mm. Texture: Densely pubescent with short strigose hairs. Color: 144A to 144B.

*Bud*.—Quantity per plant: Approximately 8. Shape: Flattened globular with immature ray florets nearly erect. Length: Approximately 1.5 cm. Diameter: Approximately 3.0 cm. Color: Outer ray florets of 154D with bud center of 143A.

*Ray florets*.—Quantity per inflorescence: Approximately 21. Arrangement: In a single whorl, slightly imbricate. Aspect: Perpendicular to disc, subtending with age, twisting absent. Shape: Elliptic to narrowly obovate. Appearance: Dull. Margin: Entire. Apex: Emarginate to notched. Base: Attenuate. Length: Approximately 4.3 cm. Width: Approximately 1.3 cm. Texture of upper and lower surfaces: Glabrous, ribbed longitudinally. Color of upper surface when first open: 14A. Color of lower surface when first open: 11C. Color of upper surface when fully open: 12A fading to 12B with age. Color of lower surface when fully open: 11D.

*Disc florets*.—Disc diameter: Approximately 3.5 cm. Disc height: Approximately 2.2 cm. Quantity per inflorescence: Approximately 300. Arrangement: Spirally arranged in center of inflorescence. Shape: Tubular. Margin of free portion: Entire. Apex: Five acute tips. Base: Fused into a tube. Length: Approximately 1.2 cm. Diameter: Approximately 2.0 mm. Texture: Glabrous. Color of inner surface when first and fully open: 145C. Color of outer surface when first and fully open: 145B transitioning to 155D at base.

*Receptacle*.—Shape: Conical. Height: Approximately 1.0 cm. Diameter: Approximately 1.5 cm. Color: 155D.

*Phyllaries*.—Quantity per inflorescence Approximately 40. Arrangement: In a three whorls. Appearance: Dull, stiff. Shape: Narrowly ovate to lanceolate, strongly curved towards the peduncle. Margin: Entire. Apex: Acute. Base: Truncate. Length: Approximately 1.0 cm. Width: Approximately 2.0 to 3.0 mm. Texture of upper or inner surface: Glabrous. Texture of lower or outer surface: Moderately pubescent with short strigose hairs. Color of upper surface: 137A. Color of lower surface: 137B.

*Receptacle spines*.—Number of spines per disc: Approximately 300. Shape: Acicular. Length: Approximately 1.4 cm. Width at widest point: Approximately 2.0 mm. Apex: Acute. Base: Truncate. Texture: Glabrous. Color: Apex of 163B, midsection of 144A, and base of 155D.

*Reproductive organs*.—Androecium: Present on disc florets only. Stamen quantity: 5 per floret. Anther shape: Oblong, basifixed. Anther length: Approximately 3.0 mm. Anther color: Closest to 203B. Filament length: Approximately 2.0 mm. Filament color: 155D. Pollen amount: Sparse to moderate. Pollen color: 17B. Gynoecium: Present on disc florets only. Pistil quantity: 1 per floret. Pistil length: Approximately 1.2 cm. Stigma shape: Bifid. Stigma length: Approximately 2.0 mm. Stigma color: 154C. Style length: Approximately 6.0 mm. Style color: 145C. Ovary length: Approximately 4.0 mm. Ovary color: 155D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balsomemyim', substantially as herein illustrated and described.

* * * * *